United States Patent [19]

Anic et al.

[11] Patent Number: 4,941,921

[45] Date of Patent: Jul. 17, 1990

[54] METHOD OF ADDING BORIC ACID OF A BORATE TO A MIXING CER-1 OR REACTION ZONE

[75] Inventors: Jure Anic, Krefeld, Fed. Rep. of Germany; Walburga Dederichs, Brussels; Lucas E. A. Huybrechts, Kontich, both of Belgium; Harry Johnson, Stockport, England

[73] Assignee: Cerestar Holding DV, Vilvoorde, Belgium

[21] Appl. No.: 295,815

[22] Filed: Jan. 11, 1989

[30] Foreign Application Priority Data

Jan. 11, 1988 [GB] United Kingdom ............... 8800502

[51] Int. Cl.$^5$ .............................................. C08L 3/00
[52] U.S. Cl. .................................... 106/213; 127/33; 127/71
[58] Field of Search ...................... 106/213; 127/33, 71

[56] References Cited

U.S. PATENT DOCUMENTS

| | | | |
|---|---|---|---|
| 1,786,417 | 12/1930 | Alexander | 106/210 |
| 2,238,767 | 4/1941 | Bauer et al. | 106/213 |
| 2,935,377 | 5/1960 | Jones | 127/33 |
| 3,137,592 | 6/1964 | Protzman | 127/71 |
| 3,228,781 | 1/1966 | Halpert | 106/213 |
| 3,288,781 | 1/1966 | Hunter | 536/23 |
| 3,312,559 | 4/1967 | Young | 106/213 |
| 3,632,786 | 1/1972 | Nickerson | 106/213 |
| 4,332,609 | 1/1982 | Ott | 71/27 |

FOREIGN PATENT DOCUMENTS 2363623 3/1978 France .
2016446 9/1979 United Kingdom .

OTHER PUBLICATIONS

Chem. Abst. 53: 2919b "Chelation of Boric Acid with Hexoses", Antikainen, 1958.

*Primary Examiner*—Paul Lieberman
*Assistant Examiner*—Helene Klemanski
*Attorney, Agent, or Firm*—Cushman, Darby & Cushman

[57] ABSTRACT

A process which includes the step of adding boric acid or a borate such as borax to a mixing or reaction zone e.g. to a starch glue preparation in which the boric acid or borate is added in the form of a liquid composition containing monoethanolamine or a polyhydroxyorganic compound such as glucose and optionally but preferably water.

18 Claims, No Drawings

METHOD OF ADDING BORIC ACID OF A BORATE TO A MIXING CER-1 OR REACTION ZONE

The present invention relates to a method of adding boric acid or a borate, especially borax decahydrate, to a mixing or reaction zone. In particular it relates to the addition of borax decahydrate or boric acid to an aqueous starch composition in the manufacture of starch glues.

Boric acid and borates eg borax pentahydrate, sodium pentaborate decahydrate, sodium metaborate octahydrate, potassium tetraborate tetrahydrate, potassium pentaborate octahydrate and especially, borax decahydrate are substances which are widely used commercially either as raw materials for the manufacture of boron-containing products or as ingredients of compositions in which they may be major or minor components. Products containing such boron compounds include cosmetics, pharmaceuticals, leather finishing agents, textile finishing agents, detergents and adhesives, particularly starch and casein adhesives.

The use of these boron compounds as raw materials or as components of a mixture frequently involves their addition in solid form and in many processes this addition is carried out continuously. The techniques used for metering such finely divided solids are well known and include, for example the use of a worm screw device.

We are particularly interested in the production of adhesives, especially starch based adhesives in which boric acid or borax decahydrate is metered continuously into the adhesive which is essentially an aqueous starch composition. The conventional method of adding the boric acid or borax decahydrate is as a solid from a hopper via a screw-feeder. In so doing however we have repeatedly encountered the problem of the solid boric acid or borax decahydrate forming lumps which either stop the feed altogether or cause an uneven addition of the boric acid or borax decahydrate. The cause of the lump formation we attribute to the hygroscopic nature of boric acid and borax decahydrate combined with the high humidity arising from the aqueous starch composition to which the boric acid or borax decahydrate is being added.

The difficulties described in the preceding paragraph would be avoided if the boric acid or borax decahydrate could be added as a solution because the metering of liquids in a continuous manner is technically easier than the metering of solids. As in many applications the boron compound is being added to a composition which includes water it would be preferable to add the boron compound in aqueous solution. Unfortunately, the solubility of such boron compounds in water is not high enough to make this possible since in the case of starch adhesives for example the total water present has an upper limit and as a large part of this water must be associated with the starch only a relatively small amount is available to solubilise the boric acid or borax decahydrate. The solubility of boric acid and borax decahydrate is 4% at 20° C. rising to about 17% at 60 to 80° C. and 29% (boric acid) and 34% (borax decahydrate) at 100° C. These solubility figures are too low for wholly aqueous solutions to be used because it is necessary that the solubility be at least 10% by weight preferably at least 15% by weight at the mixing temperatures in the range 20 to 40° C. to avoid excessive water levels in the final starch adhesive composition and thereby to reduce the capital cost of storage installations and to reduce the cost of transport to users.

We have now found, after extensive investigation, that boric acid and borates such as borax decahydrate may be added in liquid form to a reaction or mixing zone in the form of a liquid composition containing monoethanolamine or a polyhydroxyorganic compound and, optionally, water. We have also found that in the case of starch adhesives, far from having any adverse effect on the adhesive the polyhydroxyorganic compound in particular confers an enhancement of certain desirable properties. Although our investigation has been concerned with starch adhesives we believe that our invention has a wider applicability and may be considered for any application in which boric acid or a borate is to be metered and in which monoethanolamine or a polyhydroxy organic compound will have no adverse effect.

Although the solubility of boric acid and borax in various polyhydroxyorganic compounds such as glycerol has been reported and although the titration of boric acid with a strong base is recommended to be carried out in the presence of mannitol or glycerol we are not aware of any description of the practical application of boric acid or borate/polyhydroxyorganic compound compositions to facilitate the controlled addition of boric acid or a borate to a reaction or mixing zone particularly when such addition takes places in a continuous or semi-continuous manner.

British patent specification No. 2 016 446 describes the use of complexes formed by heating boric acid and a di- or polyhydroxy compound in the preservation of bacteriological specimens in which the complex is added to a sample in place of boric acid so that the composition of the sample is preserved pending analysis but the complexes are formed by heating at 80° C. to 160° C. and contain at most 20% boron.

There also exist patents which describe starch or dextrine adhesive compositions which contain borax and a polyhydroxy compound. U.S. Pat. No. 2 238 767 which is concerned with "re-moistening" adhesives provides for the presence of borax and a hydroxyl-containing plasticiser which has the function of inhibiting the insolubilising action of the borax on the special root starch conversion product used in the composition. This U.S. patent does not describe the use of the hydroxyl-containing plasticiser as a medium for the controlled addition of the borax and in all the Examples of the patent the ingredients are added separately to a batch reaction. U.S. Pat. No. 1 786 417 also describes a starch adhesive composition in which borax is present with diethylene glycol the latter acting as plasticiser. The diethylene glycol is not however used to facilitate the controlled addition of the borax and in the Examples it is added as the final ingredient to a composition already containing the borax. U.S. Pat. No. 3 228 781 describes a plant lay-out for the production of starch-based adhesives in which one plant storage vessel contains "liquid borax" which is fed to the adhesive composition. There is however the explanation of the composition of the "liquid borax".

U.S. Pat. No. 4 332 609 describes a boron-containing fertiliser in which the problem of distributing small amounts of boron evenly over a given area of soil is said to be solved by providing the boron as a complex of a boric acid with an amine which may inter alia be an alkanolamine. It is said in the U.S. patent that the boron complexes contemplated as fertilisers have previously been proposed in Belgian patent No. 842 649 as thread impregnation agents, as refrigeration agents, as liquid purification agents and as disinfection agents. There is no suggestion however that the complexes could be used to facilitate the metering of borax or boric acid to a reaction or mixing zone.

The present invention therefore is a process which includes the step of adding boric acid or a borate, to a mixing or reaction zone preferably in a continuous or semi-continuous manner and is characterised in that the boric acid or borate is added in the form of a liquid composition containing monoethanolamine or a polyhydroxy organic compound and, optionally, water.

The borate may be an alkali metal borate such as those described earlier in this specification especially borax decahydrate. Monoethanolamine is more suitable for use with boric acid than with borax decahydrate.

The polyhydroxyorganic compound may be diethanolamine or a tri-hydroxy to octahydroxy aliphatic compound eg triethanolamine or a sugar alcohol and is preferably a penta- or hexa-hydroxy aliphatic organic compound. In particular the polyhydroxyorganic compound may be a sugar alcohol containing five or six hydroxy groups eg. ribitol, xylitol, sorbitol or mannitol, or a pentose, hexose or hexulose eg. ribose, xylose, glucose, mannose or fructose. Another preferred class of polyhydroxy organic compounds for use in the process of the invention are certain aldose and/or ketose oligomers, particularly sucrose or oligomers derived from starch by hydrolysis. The starch hydrolysates contain glucose oligomers from DP-2 to DP-20 where the DP (degree of polymerisation) number represents the number of glucose units in the oligomer. The corresponding mixture of sugar alcohols produced by hydrogenating the starch hydrolysate may also be used as the polyhydroxyorganic compound as may individual hydrogenated oligomers eg. maltitol from the DP-2 oligomer maltose. In general however it is preferable to use such a composition containing as high as possible an amount of the DP1 product since when the process of the invention is to be used for the production of starch glues we have found that the lower molecular weight polyhydroxyorganic compounds give the better results.

The process of the invention is of particular utility in applications in which it is desired to add boric acid or a borate in a continuous or semi-continuous manner to a mixing or reaction zone, particularly in applications in which it is necessary to meter boric acid or a borate in a controlled manner and especially where the addition takes place under conditions of high humidity. Apart from its use in the industrial production of starch glues the process of the invention may advantageously be used in the detergent industry in the production of detergent or cleaning formulations; in the industrial formulation of liquid fertilisers, pesticides and fungicides; in the manufacture of plastics and rubbers; in the industrial production of antifreeze formulations, cutting oils, metal-treatment compositions paints; insulating and fireproofing compositions, photographic compositions and in the ceramic and glass industry.

The liquid compositions which are useful in the applications described in the preceding paragraph may contain 15% by weight or more boric acid or borate but preferably contain more than 20% especially 25% or more eg. about 35% by weight. The liquid compositions may be made by stirring the boric acid or borate with monoethanolamine or polyhydroxyorganic compound, optionally together with water, at temperatures up to 70° C. preferably at 20 to 45° C. until dissolution takes place.

The monoethanolamine or polyhydroxyorganic compound may be used alone as carrier of the boric acid or borate or it may be used together with some water, mixtures of water with the polyhydroxyorganic compound being useful when the latter is a solid or viscous liquid of high viscosity. The ratio of water to monoethanolamine or polyhydroxy compound is preferably reduced as the boric acid or borate content is increased but the amount of water may be up to about 75% of total polyhydroxyorganic compound and water. Very suitable liquid compositions for use in the invention may contain 25 to 35% by weight boric acid or borate, 55-35% by weight water and 20 to 30 weight % monoethanolamine or polyhydroxyorganic compound eg. glucose.

When the process of the invention is used for the manufacture of a starch glue the boric acid or borate is added in an amount which is 0.05 to 1.0 weight % of the final glue. The conventional starch glue is made up of a mixture of granular starch and fully gelatinised starch but more recently developed starch glues comprise starch granules partially swollen under the influence of alkali (sodium hydroxide) or a mixture of such partially swollen granules with unswollen starch granules. All these forms of glue are produced by stopping the swelling effect of the alkali by adding boric acid or another acid material eg alum (the latter together with borax-decahydrate as stabilisor), optionally together with the unswollen starch. The process of the present invention is of great utility in the continuous production of these types of starch glue comprising alkali swollen starch.

The most preferred polyhydroxyorganic compounds for use in the process of the invention are the lower molecular weight compounds particularly glucose. Thus, glucose makes possible the provision of liquid mixtures of borax decahydrate which contain 35% by weight borax decahydrate based on the total weight of the composition. Starch glues which contain a polyhydroxyorganic compound as a consequence of adding the boric acid or borax decahydrate with such compound, especially when the latter is glucose, exhibit lower viscosity levels than the equivalent composition without the polyhydroxyorganic compound. This is beneficial in as much as it enables the starch content of the glue to be increased with a corresponding improved bonding strength and less water to be evaporated. A further advantage lies in the increased penetration of the paper surface by the glue composition again with enhanced bonding strength especially when using types of paper with relatively closed surfaces. Finally, whereas the addition of solid borax to a glue preparation causes an instantaneous and significant increase in viscosity the addition in accordance with the present invention results in a less pronounced viscosity increase. Stirring of the composition is therefore correspondingly easier and there is less strain on the stirrer motor.

The invention will now be further described with reference to the following Examples.

EXAMPLE 1

Boric acid or borax decahydrate was dissolved in aqueous mixtures of glucose or sorbitol by stirring with a magnetic stirrer for 30 minutes at 25° C. The extent of the dissolution is qualitatively given in the following Table 1.

| | | Weight of | | | | |
|---|---|---|---|---|---|---|
| Experiment | boric acid | borax decahydrate | water | glucose | sorbitol | Extent of solubility |
| a | | 35 | 35 | 30 | | complete |
| b | | 25 | 50 | 25 | | complete |
| c | | 25 | 55 | 20 | | complete |
| d | | 25 | 23 | | 53 | slightly turbid but acceptable |
| e | | 20 | 24 | | 56 | complete |
| f | | 15 | 26 | | 60 | complete |
| g | | 10 | 27 | | 63 | complete |
| h | 15 | | 26 | | 60 | slightly turbid but acceptable |
| i | 10 | | 27 | | 63 | complete |

EXAMPLE 2

The viscosities and temperature stabilities of the solutions obtained in experiments (a) and (d) to (i) in Example 1 were measured. The results were as follows

| Brookfield Viscosity m Pas | (a) | (d) | (e) | (f) | (g) | (h) | (i) |
|---|---|---|---|---|---|---|---|
| 100 rpm Spindle 3 | | | | | | | |
| 23° C. | — | 640 | 445 | 320 | 275 | 140 | 160 |
| 0° C. | — | 6100 | 3450 | 2380 | 1860 | 820 | 790 |
| Solution stability at | | | | | | | |
| 23° C. | 8 | 6 | 8 | 8 | 8 | 7 | 8 |
| 8° C. | 8 | 6 | 8 | 8 | 8 | 6 | 8 |
| 0° C. | 8 | 6 | 7 | 8 | 8 | 6 | 8 |
| −10° C. | 1 | 5 | 7 | 8 | 8 | 5 | 8 |
| −18° C. | 1 | 4 | 7 | 8 | 8 | 5 | 8 |

*The stability was assessed visually from 1 = heavy crystallisation to 8 = clear and stable solution. For practical application 5 to 8 is acceptable.at*

EXAMPLE 3

A conventional "Stein Hall" starch glue was prepared by mixing together 320 mls water, 35 grams granular corn starch and 5.3 grams sodium hydroxide dissolved in 49 mls water. The mixture was heated to gelatinise the "carrier" starch and, after cooling to 35° C. by adding a further 480 mls water, 192 grams granular corn starch were added together with either (a), 5.3 grams borax decahydrate or, (b), 15.1 grams of a solution of borax decahydrate (35 wt %), glucose (30 wt %) and water (35 wt %). The Stein Hall viscosities, Brookfield Viscosities and Gel Temperatures of the compositions were as follows:

| Stein-Hall Viscosity (seconds) at 35° C. | (a) | (b) |
|---|---|---|
| initial | 90 | 45 |
| 1 hour | 145 | 72 |
| 3 hours | 149 | 62 |
| overnight | 128 | 53 |
| Brookfield Viscosity RVT mPas Spindle 3 | | |
| initial | 290 | 230 |
| 1 hour | 410 | 370 |
| 3 hours | 410 | 330 |
| overnight | 380 | 290 |
| Gel Temperature (°C.) | 63 | 63 |

The results show that lower viscosity glues are obtained with the same amount of starch using the process of the invention as compared with the prior art process.

EXAMPLE 4

A partially swollen (gelatinised) starch glue was prepared by warming 767 mls water, 106 grams granular corn starch and 5.6 grams sodium hydroxide (dissolved in 12 mls water). When the starch had swollen to give a viscosity of the mixture of 400 mPas 106 grams of granular corn starch was added together with either, (a), 3.5 grams borax decahydrate or, (b), 10 grams of a solution of borax decahydrate (35 wt %), glucose (30 wt %) and water (35 wt %). The SteinHall and Brookfield viscosities and gel temperatures of the compositions were as follows:

| Stein-Hall Viscosity (seconds) at 35° C. | (a) | (b) |
|---|---|---|
| initial | 33 | 29 |
| 1 hour | 34 | 30 |
| 3 hours | 37 | 31 |
| overnight | 52 | 33 |
| Brookfield Viscosity RVT mPas Spindle 3 | | |
| initial | 440 | 360 |
| 1 hour | 490 | 390 |
| 3 hours | 560 | 420 |
| overnight | 830 | 520 |
| Gel Temperature (°C.) | 58 | 59 |

As in Example 3 the viscosity of the composition prepared in accordance with the process of the present invention has a lower viscosity than the viscosity of the similar prior art composition.

EXAMPLE 5

The technique used in Example 1 was repeated but the borax decahydrate was replaced by borax pentahydrate and the polyhydroxyorganic compound was sorbitol. The results were as follows and indicate that stable adhesives incorporating borax pentahydrate can be made using the process of the invention:

| Weight % Concentration of borax pentahydrate | 0 | 10 | 15 |
|---|---|---|---|
| Brookfield RVT Viscosity (mPas, 100 rpm, 23° C.) | 205 | 435 | 650 |
| Solution stability at 23° C. | 8 | 6 | 6 |

We claim:

1. A process which includes the step of adding boric acid or a borate to a mixing or reaction zone, wherein the boric acid or borate is added in the form of a liquid composition containing monoethanolamine or a polyhydroxyorganic compound selected from the group consisting of a sugar alcohol, a pentose, a hexose, a hexulose, sucrose, starch hydrolysates and hydrogenated starch hydrolysates.

2. A process according to claim 1, wherein the borate is borax decahydrate.

3. A process according to claim 1 or claim 2, wherein the polyhydroxyorganic compound is a trihydroxy to octahydroxy aliphatic compound.

4. A process according to claim 1, wherein the polyhydroxyorganic compound is glucose.

5. A process according to claim 1 or claim 2 characterised in that boric acid or borax decahydrate is added to a mixing zone in which a starch glue is in process of preparation.

6. A process according to claim 1 or claim 2 characterised in that the liquid composition contains more than 20% by weight boric acid or borate.

7. A liquid composition for use in the process of claim 1 or claim 2 characterised in that it comprises monoethanolamine or a polyhydroxyorganic compound and, optionally, water and contains 15% by weight or more boric acid or a borate and has been prepared by dissolving the boric acid or borate in the monoethanolamine or polyhydroxyorganic compound and optional water at a temperature up to 70° C.

8. A liquid composition according to claim 7, wherein it comprises 25 to 35% by weight boric acid or borate, 55 to 35% by weight water and 20 to 30% by weight monoethanolamine or polyhydroxyorganic compound.

9. A liquid composition according to claim 7 in which the amount of boric acid or borate is more than 20% by weight.

10. A process according to claim 1 or claim 2, wherein boric acid or borax decahydrate is added to a mixing zone in which a starch glue is in process of preparation.

11. A process according to claim 10 wherein the boric acid or borax decahydrate is added in an amount which is 0.05 to 1.0% by weight of the final glue.

12. A process according to claim 1 or claim 2, wherein the liquid composition contains more than 20% by weight boric acid or borate.

13. A liquid composition according to claim 1 or claim 2, wherein the composition comprises monoethanolamine or a polyhydroxyorganic compound and contains 15% by weight or more boric acid or a borate and has been prepared by dissolving the boric acid or borate in the monoethanolamine or polyhydroxyorganic compound at a temperature up to 70° C.

14. A process according to claim 1, wherein the boric acid or borate is added to the mixing or reaction zone in a continuous or semi-continuous manner.

15. A process according to claim 1, wherein the liquid composition further contains water.

16. A liquid composition according to claim 13, wherein the composition further comprises water.

17. A liquid composition according to claim 13, wherein the composition contains more than 20% by weight of the boric acid or borate.

18. A liquid composition according to claim 13, wherein the composition has been prepared by dissolving the boric acid or borate in the monoethanolamine or polyhydroxyorganic compound and water.

* * * * *